United States Patent [19]

Cecchetti et al.

[11] Patent Number: 5,221,741
[45] Date of Patent: Jun. 22, 1993

[54] PROCESS FOR THE PREPARATION OF 9-FLUORO-10-(4-METHYL-1-PIPERAZINYL)-7-OXO-2,3-DIHYDRO-7H-PYRIDO[1,2,3-DE][1,4]BENZOTHIAZINE-6-CARBOXYLIC ACID HYDROCHLORIDE

[75] Inventors: Violetta Cecchetti, Perugia; Arnaldo Fravolini, S. Sisto; Pier Giuseppe Pagella, Fraz. Catraglia; Fausto Schiaffella, Perugia, all of Italy

[73] Assignee: Mediolanum Farmaceutici S.p.A., Milan, Italy

[21] Appl. No.: 889,797

[22] Filed: May 29, 1992

[30] Foreign Application Priority Data

Jun. 7, 1991 [IT] Italy ............... MI91 A 001577

[51] Int. Cl.$^5$ ............... C07D 513/04
[52] U.S. Cl. ............... 544/34
[58] Field of Search ............... 544/34

[56] References Cited

U.S. PATENT DOCUMENTS 4,668,784  5/1987  Mascellani et al. ............... 544/32

FOREIGN PATENT DOCUMENTS

165375B1  12/1985  European Pat. Off. .
0275971    7/1988  European Pat. Off. .
2217710    1/1989  United Kingdom .

OTHER PUBLICATIONS

Chemical Abstracts, vol. 108, No. 19, May 9, 1988; p. 654, Abstract No. 167489b, Columbus, OH, US & JP-A-62 216 591 (Dainippon Pharmaceutical Co., Ltd.) Sep. 22, 1987.

Synthetic Communications, vol. 21, N. 22, 1991; pp. 2301-2308, Marcel Dekker, Inc., New York, US; V. Cecchetti et al.: "One-pot synthesis of rufloxacin".

Cecchetti et al.; "Quinolonecarboxylic Acids. 2. Synthesis and Antibacterial Evaluation of 7-oxo-2,3-dihydro-7H-pyrido[1,2,3-de][1,4]benzothiazine-6-carboxylic acids"; J. Med. Chem., 1987, 30, 465.

Drugs of the Future, vol. 15, No. 7, 1990, pp. 762-767.

Primary Examiner—John M. Ford
Attorney, Agent, or Firm—Oliff & Berridge

[57] ABSTRACT

Process for the preparation of 9-fluoro-10-(4-methyl-1-piperazinyl)-7-oxo-2,3-dihydro-7H-pyrido[1,2,3-de][1,4]benzothiazine-6-carboxylic acid hydrochloride (Rufloxacin) by reaction of 2,3,5-trifluoro-4-(4-methyl-1-piperazinyl)benzoyl ethyl acetate with N,N-dimethylformamide dimethylacetal, followed by reaction with 2-aminoethanethiol, intramolecular cyclization by treatment with NaH, hydrolysis with H$_2$O and salification with HCl.

5 Claims, No Drawings

PROCESS FOR THE PREPARATION OF 9-FLUORO-10-(4-METHYL-1-PIPERAZINYL)-7-OXO-2,3-DIHYDRO-7H-PYRIDO[1,2,3-DE][1,4-]BENZOTHIAZINE-6-CARBOXYLIC ACID HYDROCHLORIDE

PRIOR ART 9-fluoro-10-(4-methyl-1-piperazinyl)-7-oxo-2,3-dihydro-7H-pyrido[1,2,3-de][1,4]benzothiazine-6-carboxylic acid hydrochloride, also known as Rufloxacin, is a new potent quinolone antibacterial agent, which is expected to be used in single daily dose therapy (V. Cecchetti et al., *J.Med.Chem.*, 30, 465 (1987) and *Drugs Future*, 15, 763 (1990)).

The processes known so far for the preparation of Rufloxacin, as described e.g. in the aforesaid *J.Med.Chem.* and in patents EP 165375B1, Jpn Kokai Tokkyo Koho 60 208 987 and U.S. Pat. No. 4,668,784, consist of several steps which imply exacting and expensive operations including at the end the oxidation to sulphoxide of the thiazinic sulphur of ethyl 10-chloro-9-fluoro-7-oxo-2,3-dihydro-7H-pyrido[1,2,3-de][1,4]benzothiazine-6-carboxylate to yield the sulphoxide intermediate, which allows the regiospecific chlorine substitution at C-10 with 4-methylpiperazine, followed by deoxygenation with PCl3 and hydrolysis.

SUMMARY

The present invention relates to an improved and advantageous process for the preparation of 9-fluoro-10-(4-methyl-1-piperazinyl)-7-oxo-2,3-dihydro-7H-pyrido[1,2,3-de][1,4]benzothiazine-6-carboxylic acid hydrochloride (1) (Rufloxacin) consisting of the following steps:

a) 2,3,5-trifluoro-4-(4-methyl-1-piperazinyl)-benzoyl ethyl acetate (2) was caused to react with N,N-dimethylformamide dimethylacetal;

b) 2-[2,3,5-trifluoro-4-(4-methyl-1-piperazinyl)-benzoyl]-3-di-methylamino ethyl acrylate (3) obtained in a) was caused to react with 2-aminoethanethiol to give compound (4);

c) compound (4) obtained in b) was subjected to intramolecular cyclization by treatment with NaH;

d) the obtained compound (5) was then hydrolyzed and salified with HCl to give compound (1).

This process has the advantage that the envisaged reactions can be carried out in a single reactor without intermediates separation (overall yield: approx. 70%).

DETAILED DESCRIPTION OF THE INVENTION

The characteristics and advantages offered by the process for the preparation of 9-fluoro-10-(4-methyl-1-piperazinyl)-7-oxo-2,3-dihydro-7H-pyrido[1,2,3-de][1,4]benzothiazine-6-carboxylic acid hydrochloride (1), also known as Rufloxacin, as per this invention, will be described in more detail hereinafter.

The starting material was 2,3,5-trifluoro-4-(4-methyl-1-piperazinyl)-benzoyl ethyl acetate (2) and the process comprised the reactions shown below (scheme 1).

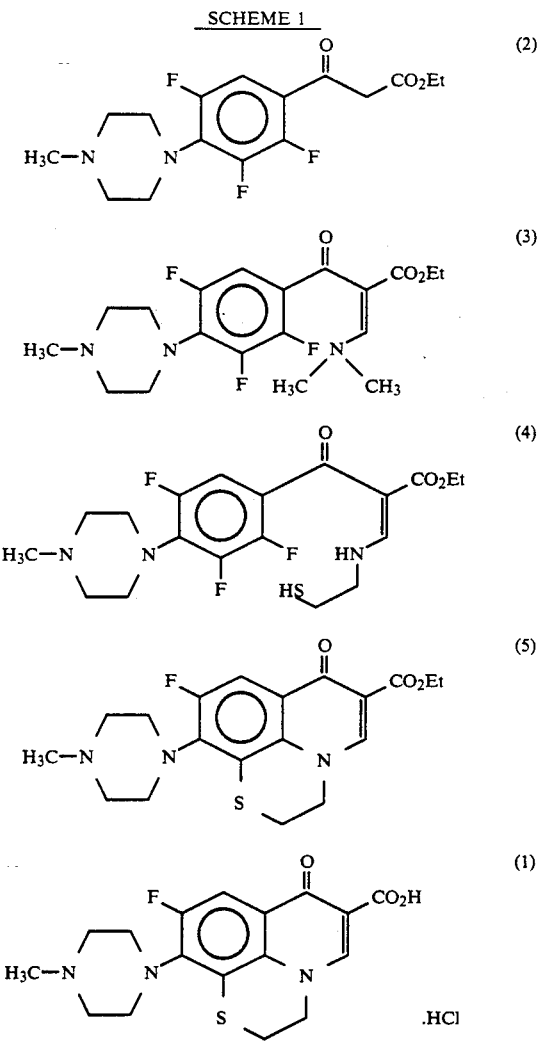

Compound (2) was dissolved in toluene and refluxed with N,N-dimethylformamide dimethylacetal in a molar ratio ranging from 1:1.3 to 1:1.8. Concentration under reduced pressure gave an oily compound (3).

Compound (3) was dissolved in ethanol, cooled to approx. 0° C. and added with 2-aminoethanethiol in a molar ratio in respect of (2) ranging from 1.2:1 to 1.5:1.

The resulting mixture was caused to react at room temperature under stirring and then concentrated under reduced pressure to give a viscous oil containing compound (4).

This product was dissolved in THF, cooled to approx. 0° C., added with NaH in a molar ratio ranging from 2:1 to 2.5:1 in respect of compound (2), and stirred for a few minutes at 0° C. in a nitrogen environment. A suspension containing compound (5) was obtained. $H_2O$ was added to secure hydrolysis by heating to reflux. The obtained product was cooled to room temperature, neutralized with 2N HCl, concentrated to dryness under reduced pressure, and taken up with ethanol. The insoluble was separated by filtration and the solution was added with an ether solution saturated with HCl. The precipitated solid was filtered and crystallized from aqueous ethanol to give compound (1), mp 322°–324° C.

All the aforesaid operations can be carried out in a single reactor without intermediates separation (overall yield: approx. 70%); otherwise, they can be carried out stepwise, with intermediates separation and characterization.

The following examples will illustrate the process of this invention: in particular, example 1 concerns the case of operations carried out in a single reactor without intermediates separation, whereas example 2 concerns the case envisaging the separation and characterization of the intermediates obtained in the various steps.

EXAMPLE 1

9-fluoro-10-(4-methyl-1-piperazinyl)-7-oxo-2,3-dihydro-7H-pyrido [1,2,3-de][1,4]benzothiazine-6-carboxylic acid hydrochloride (1)

A solution of 2,3,5-trifluoro-4-(4-methyl-1-piperazinyl)-benzoyl ethyl acetate (2) (2.0 g, 5.8 mmoles) in toluene (10 ml) was added with N,N-dimethylformamide dimethylacetal. The mixture was heated to reflux for 1 hr. and concentrated to dryness under reduced pressure to give a viscous oil which was dissolved in ethyl alcohol (20 ml).

The ethanol solution was cooled in an ice bath and added with a solution of 2-aminoethanethiol (0.6 g, 7.8 mmoles) in ethyl alcohol (5 ml). The resulting mixture was stirred at room temperature for 5 hrs. and concentrated to dryness under reduced pressure to give a viscous oil which was dissolved in anhydrous THF (30 ml).

The obtained solution was cooled in an ice bath and added with sodium hydride (60% NaOH suspension, 0.5 g, 12.5 mmoles). The resulting suspension was stirred in a nitrogen environment at 0° C. for 15 min., added with water (30 ml), refluxed for 15 min. to secure dissolution.

The solution was cooled at room temperature, neutralized with 2N HCl, and concentrated to dryness under reduced pressure. The residue was added with ethanol (20 ml) and the insoluble was separated by filtration.

The filtrate was added with a solution saturated with gaseous HCl in diethyl ether. The precipitated solid was filtered and crystallized from EtOH/H$_2$O in a 7:3 ratio to give compound (1) (overall yield 71%), mp 322°-324° C.

EXAMPLE 2

2[2,3,5-trifluoro-4-(4-methyl-1-piperazinyl)benzoyl]-3-dimethylamino ethyl acrylate (3)

A mixture of 2,3,5-trifluoro-4-(4-methyl-1-piperazinyl)benzoyl] ethyl acetate (2) (2.0 g, 5.8 mmoles) and N,N-dimethylformamide dimethylacetal (1,2 ml, 9.1 mmoles) in toluene (10 ml) was refluxed for 1 hr. and concentrated to dryness under reduced pressure. The viscous oil residue was purified by silica gel column flash chromatography eluting with CHCl$_3$.

A viscous oil (3) (2.11 g; yield 91%) consisting of a mixture of isomers (E) and (Z) (7:3 or 3:7) was obtained and used immediately in the subsequent step.

$^1$H-NMR: 1.05 and 1.10 (3H, each t, J=7 Hz, CH$_2$CH$_3$); 2.40 (3H, s, NCH$_3$); 2.50-2.70 (4H, m, CH$_2$ piperazine); 3.10 [6H, bs, N(CH$_3$)$_2$]; 3.25-3.50 (4H, m, CH$_2$ piperazine); 4.05 and 4.10 (2H, each q, J=7 Hz, CH$_2$CH$_3$); 7.00-7.30 (1H, m, H aromatic); 7.75 and 7.90 (1H, each s, H olefin).

2-[2,3,5-trifluoro-4-(4-methyl-1-piperazinyl)-benzoyl]-3-(1-mercapto-et-2-ilamino) ethyl acrylate (4)

A solution of compound (3) (2.0 g, 5.0 mmoles) in EtOH (20 ml) was cooled in an ice bath and added with a solution of 2-aminoethanethiol (0.6 g, 7.8 mmoles) in EtOH (5 ml).

The mixture was stirred at room temperature for 5 hrs. and concentrated to dryness under reduced pressure. The viscous oil residue was purified by silica gel column chromatography with CHCl$_3$ as eluent yielding a viscous oil (4) (1.7 g; yield 77%) consisting of a mixture of isomers (E) and (Z) (7:3 or 3:7).

$^1$H-NMR: 0.90-1.35 (4H, m, CH$_2$CH$_3$ and SH); 2.45 (3H, s, NCH$_3$); 2.50-2.65 (4H, m, CH$_2$ piperazine); 2.85-3.10 (2H, m, NCH$_2$CH$_2$S); 3.25-3.45 (4H, m, CH$_2$ piperazine); 3.65-3.90 (2H, m, NCH$_2$CH$_2$S); 4.05-4.10 (2H, each q, J=7 Hz, CH$_2$CH$_3$); 6.75-7.05 (1H, m, H aromatic); 7.95 and 8.05 (1H, each d, J=15 Hz, H olefin); 9.30-9.70 and 10.80-11.00 (1H, each m, NH).

9-fluoro-10-(4-methyl-1-piperazinyl)-7-oxo-2,3-dihydro-7H-pyrido [1,2,3-de][1,4]benzothiazine-6-ethyl carboxylate (5)

A solution of compound (4) (1.5 g, 3.5 mmoles) in anhydrous THF (30 ml) was cooled in an ice-water bath and slowly added with 60% NaH in oily suspension (0.35 g, 8.75 mmoles). The reaction mixture was stirred for 15 min. at 0° C. in a nitrogen environment, poured into ice-water (100 ml), and extracted with CHCl$_3$. The organic phase was separated, washed with H$_2$O and, after water elimination with sodium sulphate, evaporated to dryness.

The solid residue was crystallized from ethyl acetate to give 1.2 g (yield 88%) of compound (5), mp 160°-163° C.

$^1$H-NMR: 1.40 (3H, t, J=7 Hz, CH$_2$CH$_3$); 2.35 (3H, s, NCH$_3$); 2.50-2.70 (4H, m, CH$_2$ piperazine); 3.05-3.50 (6H, m, CH$_2$ piperazine and NCH$_2$CH$_2$S); 4.35 (2H, q, J=7 Hz, CH$_2$CH$_3$); 4.50-4.75 (2H, m, NCH$_2$CH$_2$S); 7.80 (1H, d, J=12 Hz, H aromatic); 8.30 (1H, s, H olefin).

9-fluoro-10-(4-methyl-1-piperazinyl)-7-oxo-2,3-dihydro-7H-pyrido[1,2,3-de][1,4]benzothiazine-6-carboxylic acid hydrochloride (1)

A suspension of compound (5) (0.2 g) in NaOH (15% by wt.; 10 ml) was heated to reflux for 15 min.; the mixture was then cooled at room temperature, neutralized with acetic acid, and evaporated to dryness under reduced pressure. EtOH (10 ml) was added to the solid residue and the insoluble residue was separated by filtration. The filtrate was added with a solution saturated with HCl in diethyl ether. The obtained precipitate was separated by filtration and crystallized from EtOH/H$_2$O in a 7:3 ratio to give 0.16 g of compound (1) (yield 86%).

We claim:

1. A process for the preparation of 9-fluoro-10-(4-methyl-1-piperazinyl)-7-oxo-2,3-dihydro-7H-pyrido[1,2,3-de][1,4]benzothiazine-6-carboxylic acid hydrochloride (Rufloxacin) comprising the steps of:

a) reacting 2,3,5-trifluoro-4-(4-methyl-1-piperazinyl)-benzoyl ethyl acetate with N,N-dimethylformamide dimethylacetal to obtain 2-[2,3,5-trifluoro-4-(4-methyl-1-piperazinyl)-benzoyl]-3-dimethylamino ethyl acrylate;

b) reacting said 2-[2,3,5-trifluoro-4-(4-methyl-1-piperazinyl)-benzoyl]-3-dimethylamino ethyl acrylate with 2-aminoethanethiol to obtain 2-[2,3,5-trifluoro-4-(4-methyl-1-piperazinyl)-benzoyl]-3-(1-mercapto-et-2-ilamino) ethyl acrylate;

c) subjecting said 2-[2,3,5-trifluoro-4-(4-methyl-1-piperazinyl)-benzoyl]-3-(1-mercapto-et-2-ilamino) ethylacrylate to intramolecular cyclization by treatment with NaH to obtain 9-fluoro-10-(4-methyl-1-piperazinyl)-7-oxo-2,3-dihydro-7H-pyrido[1,2,3-de][1,4]benzothiazine-6-ethyl carboxylate; and d) hydrolyzing and salifying said 9-fluoro-10-(4-methyl-1-piperazinyl)-7-oxo-2,3-dihydro-7H-pyrido[1,2,3-de][1,4]benzothiazine-6-ethyl carboxylate with HCl to obtain said 9-fluoro-10-(4-methyl-1-piperazinyl)-7-oxo-2,3-dihydro-7H-pyrido[1,2,3-de][1,4]benzothiazine-6-carboxylic acid hydrochloride.

2. The process as per claim 1 wherein the said steps are carried out in a single reactor without intermediates separation.

3. The process as per claim 1 wherein step a) is carried out in toluene in a molar ratio of 2,3,5-trifluoro-4-(4-methyl-1-piperazinyl)-benzoyl ethyl acetate to said N,N-dimethylformamide dimethylacetal ranging from 1:1.3 to 1:1.8, at heating to reflux.

4. The process as per claim 1 wherein step b) is carried out in ethanol in a molar ratio of said 2-aminoethanethiol to 2,3,5-trifluoro-4-(4-methyl-1-piperazinyl)-benzoyl ethyl acetate ranging from 1.2:1 to 1.5:1, at room temperature.

5. The process as per claim 1 wherein reaction c) is carried out in THF in a molar ratio of said NaH to 2,3,5-trifluoro-4-(4-methyl-1-piperazinyl)-benzoyl ethyl acetate ranging from 2:1 to 2.5:1 in a nitrogen environment and at a temperature of 0° C.

* * * * *